United States Patent
Osada

[11] Patent Number: 6,162,236
[45] Date of Patent: Dec. 19, 2000

[54] TROCAR NEEDLE AND EXPANDABLE TROCAR TUBE

[75] Inventor: Toshihiko Osada, Kanagawa-ken, Japan

[73] Assignee: Terumo Kabushiki Kaisha, Tokyo, Japan

[21] Appl. No.: 08/891,934

[22] Filed: Jul. 14, 1997

Related U.S. Application Data

[63] Continuation of application No. 08/500,061, Jul. 10, 1995, abandoned.

[30] Foreign Application Priority Data

Jul. 11, 1994 [JP] Japan ................................. 6-157733
Nov. 17, 1994 [JP] Japan ................................. 6-283142

[51] Int. Cl.⁷ .................................................. A61B 17/34
[52] U.S. Cl. ..................... 606/185; 604/264; 604/272; 606/191
[58] Field of Search ................................. 604/164, 264, 604/272; 606/184, 185, 190–200; 600/204, 207

[56] References Cited

U.S. PATENT DOCUMENTS

| | | |
|---|---|---|
| 4,846,791 | 7/1989 | Hattler et al. ........................... 604/43 |
| 5,209,736 | 5/1993 | Stephens et al. . |
| 5,263,937 | 11/1993 | Shipp ...................................... 604/264 |
| 5,320,611 | 6/1994 | Bonutti et al. ........................... 604/264 |
| 5,389,077 | 2/1995 | Melinyshyn et al. .................... 604/264 |
| 5,431,676 | 7/1995 | Dubrul et al. ........................... 606/185 |
| 5,562,677 | 10/1996 | Hildwein et al. ....................... 606/185 |

FOREIGN PATENT DOCUMENTS

| | | |
|---|---|---|
| 0 150 281 | 8/1985 | European Pat. Off. . |
| 0 535 974 | 4/1993 | European Pat. Off. . |

*Primary Examiner*—Glenn K. Dawson
*Attorney, Agent, or Firm*—Burns, Doane, Swecker & Mathis, LLP

[57] ABSTRACT

A trocar including a trocar tube and a trocar needle inserted into the trocar needle. The trocar tube has a tubular portion and a grip attached to the rear end of the tubular portion. The front end of the trocar tube is smaller in diameter than the rear end. The front end portion of the trocar tube can be expanded by inserting an expanding device of an inside diameter suited to the outside diameter of an operative device inserted. The trocar needle has a shaft a piercing end provided at the front side of the shaft, and a grip attached to the rear end of the shaft. The shaft becomes gradually smaller in diameter toward the front end.

28 Claims, 5 Drawing Sheets

TROCAR NEEDLE AND EXPANDABLE TROCAR TUBE

This application is a continuation of application Ser. No. 08/500,061, filed Jul. 10, 1995 now abandoned.

BACKGROUND OF THE INVENTION

This invention relates to a trocar used for introducing an endoscope, forceps, electric cautery or other device into a body cavity in surgery under the endoscope.

In recent years, surgery under the endoscope which excises the gallbladder or anastomose the intestine without incision of the abdomen is performed in practice. This technique is a low-invasion surgery without incision of the abdomen. Therefore, a long hospitalization is not needed and the burden of a patient is light.

A trocar is a surgical instrument used for puncturing the abdomen and inserting an endoscope, forceps, electric cautery, or other surgical instrument into the abdomen, and typically comprises a trocar tube (cannula) and a trocar needle (blade) with a sharp-pointed front end. When used, a trocar with the trocar needle held in the trocar tube is thrust into the abdominal cavity through the body wall with the front end of the trocar needle (blade), and then the blade alone is pulled out leaving the trocar tube to permit the insertion of a surgical device such as an endoscope, forceps, or electric cautery into the abdominal cavity.

Figure 12:
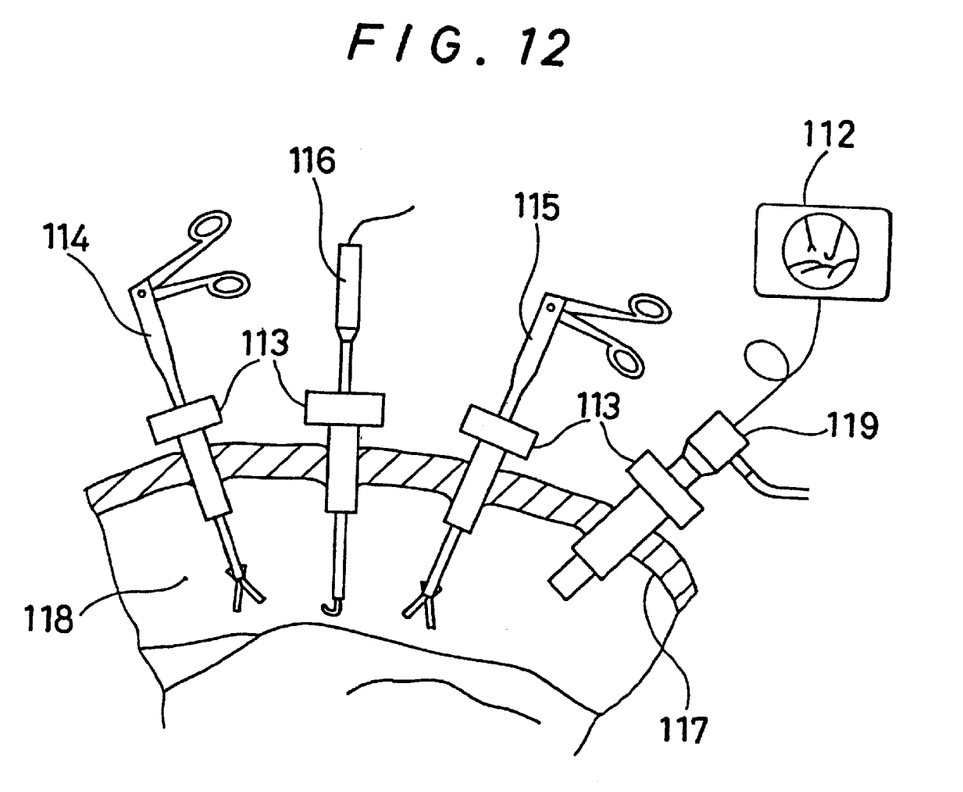
FIG. 12 is a sectional view which illustrates the technique of surgery under the endoscope conventionally performed.

Surgery under the endoscope conventionally perzbrmed is described here using FIG. 12, a sectional view which illustrates the technique of surgery under the endoscope. In surgery under the endoscope, a space for operation is made in the abdominal cavity 118 by stabbing an air-injecting needle through the body wall 117 and injecting a gas such as $CO_2$ to inflate the abdominal cavity or by skewering the body wall with a wire and pulling up the body wall. Next, a small incision is made in the body wall 117, and a trocar is thrust into the incision and the trocar needle (not shown) is pulled out leaving the trocar tube. Then, an endoscope 119 such as a flexible or rigid scope is inserted into the abdominal cavity 118 through the path secured by means of the trocar tube 113. Long operative devices such as a forceps 114, grasping forceps 115, and electric cautery 116 are also inserted through the paths secured by means of trocar tubes 113 in the same manner, and excision of the gallbladder or anastomosis of the bowel is performed watching the image on the monitor screen taken by the endoscope.

This type of trocar tube is conventionally made of a high-rigidity material such as a stainless steel or hard resin. Therefore, devices which can pass through the trocar tube are limited to slender rod-like devices with a dianmeter or breadth smaller than the inside diameter of the trocar tube.

On the other hand, a flexible trocar tube which is made of a resilient material and permits the insertion of a curved device is described in E.P.A. 535,974.

Although this trocar tube makes the insertion of a curved device through it possible, the one with an inside diameter suited to the outside diameter of the device inserted must be used, because the inside diameter is uniform throughout the length. A surgeon stabs a plurality of trocar tubes of different diameters suited to the operative devices used for the operation into the body cavity beforehand according to the contents of the operation performed. It sometimes happens that the inside diameter of some trocar tube is too small to insert an operative device or to take out the excised organ or tissue. In that case, a trocar tube of a laraer inside diameter must be stabbed, causing the problems that the number of the trocar tubes used increases, that the time required for the operation is prolonged, and that the operation becomes troublesome.

Further, since the trocar tube has a diameter sufficiently large to permit the insertion of operative devices at its front end, the front end of the trocar tube receives a considerable resistance when the trocar is thrust into the body wall hindering the thrust, and an excoriation about the same size as the diameter is left.

This invention was made to solve these problems with conventional trocars.

The first object of this invention is to provide a low-invasion trocar tube through which various operative devices can be inserted, is easy to thrust into the body wall, and does not leave a large excoriation, and a trocar equipped with such a trocar tube. Further, since conventional trocars are constructed so that only the pointed end portion of the inner needle projects from the trocar tube when the trocar needle is put in the trocar tube coaxally, they have problems that the front end of the trocar tube catches on the body wall and pulls in the body wall, causing a large resistance to the thrust when the trocar is thrust into the body wall.

The second object of this invention is to provide a trocar needle which is less invasive, exerts a smaller pulling force on the body wall, and has a smaller resistance to the thrust, and also to provide a trocar equipped with the trocar needle.

SUMMARY OF THE INVENTION

The aforementioned first object is solved by a trocar tube of this invention and a trocar equipped with the trocar tube.

The trocar tube of this invention comprises a tubular portion and a grip attached to a rear end of the tubular portion, and the tubular portion is smaller in diameter at a front end than at the rear end in the usual state, and a front end portion of the tubular portion can expand when a device having an outside diameter greater than an inside diameter of the front end of the tubular portion is inserted.

The trocar of this invention comprises a trocar tube which comprises a tubular portion and a grip attached to a rear end of the tubular portion, the tubular portion being smaller in diameter at a front end than at the rear end in the usual state, and a front end portion of the tubular portion being able to expand when a device having an outside diameter greater than an inside diameter of the front end of the tubular portion is inserted, and a trocar needle which comprises a shaft, a piercing end provided at the front end side of the shaft, and a grip member attached to the rear side of the shaft, the shaft becoming gradually smaller in diameter toward the front end and having a neck for supporting the front end of the trocar tube formed at a rear of the piercing end substantially of a cone which becomes gradually smaller from the rear end to the front end and is closely similar to a form of a lumen of the trocar tube in the usual state.

The aforementioned second object is solved by a trocar needle of this invention.

The trocar needle of this invention comprises a shaft, a piercing end provided at the front side of the shaft, and a needle grip attached to the rear end of the shaft, and the shaft becomes gradually smaller in diameter toward the front end and has a neck for supporting the front end of the trocar tube formed at the rear of the piercing end.

DETAILED DESCRIPTION OF THE PREFERRED EMBODIMENTS

A trocar tube of this invention is described below in detail using the preferred embodiments shown in the drawings.

Figure 1:
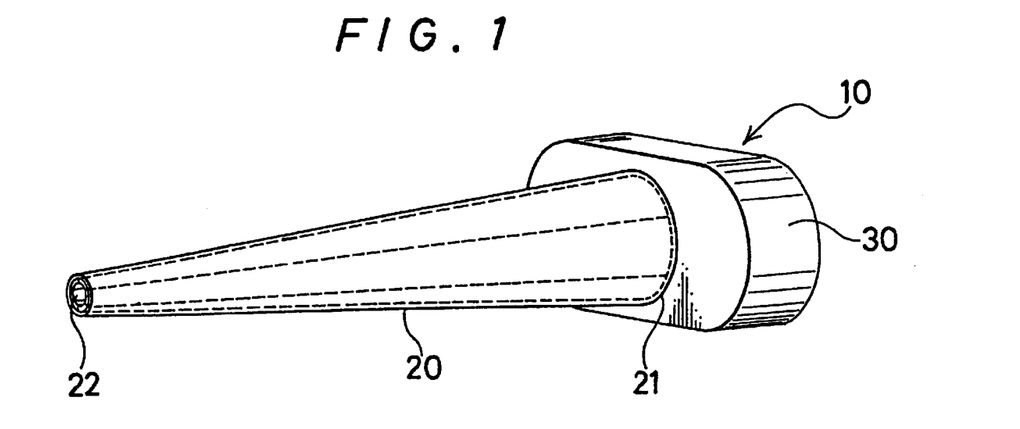
FIG. 1 is a perspective view of an embodiment of a tube of this invention.

FIG. 1 is a perspective view of an embodiment of the trocar tube of this invention in the state when not used. As shown in this Figure, the trocar tube 10 of this invention comprises a tubular portion 20 and a grip 30 attached to the rear end 21 of the tubular portion 20. The tubular portion 20 is usually made in the ibrm of a substantial cone the diameter of the front end 22 of which is smaller than that of the rear end 21. Although the trocar tube 10 of this embodiment is made in a conical form, it may be made in a substantial pyramidal form the diameter of the front end of which is smaller than that of the rear end or a form resembling a pyramid.

The front end 22 of the trocar 10 is constructed so that its inside diameter can be expanded to the outside diameter of a expanding device later described. When a device whose functioning parts (cutting or clamping parts, for example) and shafts are made of a rigid material and have an almost uniform outside diameter, such as a forceps, is inserted, the front end 22 of the trocar tube 10 can be expanded without using the expanding device. Thus the lumen 25 of the tubular portion 20 can be expanded according to the external shape of the device inserted or the expanding device. In other words, the tubular portion 20 is made so that the sectional area of the lumen 25 near the front end 22 can expand. Specifically, the sectional area of the lumen 25 of the front end 22 can be expanded up to almost the same area as the lumen 25 of the rear end 21, that is, the inside diameter of the front end 22 of the tubular portion 20 can be extended up to almost the same length as that of the rear end 21. The front end 22 of the tubular portion 20 is also made so that it resumes the original inside diameter after the device is pulled out. The tubular portion 20 comprises a plurality of strips 23 which are arranged in a ring or a tube and an outer tube 24 which covers the outside surface of the strips. The strips 23 are thus arranged in a ring, but the sides of adjacent strips are not secured to each other. Therefore, when the device is inserted into the lumen 25, the sides of adjacent strips 23 come apart, and the front end 22 of the trocar tube 10 expands. The strips 23 are of a trapezoid the width of the front end of which is larger than that of the rear end. The outer tube 24 has an elasticity and thereby prevents injury from being inflicted on the body wall when the trocar tube 10 is thrust into the abdominal cavity and retains airtightness.

There is no special limitation on the material for the strips 23 except that the material has a strength able to withstand the force which the tubular portion 20 receives when the front end of the tubular portion 20 catches on the body wall and the pressure from the body wall. Metallic materials such as stainless steel, an aluminum alloy, a super high-resilience metal and a shape-memory alloy and synthetic resins such as polyamide, poly(vinyl chloride), polycarbonate, ABS (acrylonitrile butadiene styrene copolimer), polyethylene, polypropylene, fluorocarbon resin and acrylic resin can be enumerated for example. The aibrementioned synthetic resins which are not electrically conductive are preferable, and polycarbonate and ABS are specially preferable, taking into account the use of electric devices such as an electric cautery.

The thickness of the strips 23 is within the range of about 0.05 to 3.0 mm, preferably about 0.1 to 1.5 mm, and is especially preferably about 0.5 mm, though it depends on the material used. If the thickness of the strips 23 is greater than 0.05 mm, the trocar tube may be able to withstand the pressure of the body wall and if smaller than 3.0 mm, the trocar is easy to thrust into the body wall because of the increased resistance.

The width of the front end of the strips 23 depends on the number of the strips 23 forming the tubular portion 20. When the number of the strips 23 is six, for example, the width of the front end is equal to or smaller than about 6.0 mm, preferably about 4.0 mm, and is especially preferably about 1.5 mm. If the width of the front end of the strips 23 is smaller 6.0 mm, the outside diameter of the front end 22 of the tubular portion 20 does not become too large and the trocar is easy to therst into the body wall.

The width of the rear end of the strips 23 also depends on the number of the strips 23 forming the tubular portion 20. When the number of the strips 23 is six, for example, the width of the rear end is equal to or smaller than about 3.0 to 50 mm, preferably about 5.0 to 20 mm. About 6.0 mm is especially preferable. If the width of the rear end of the strips 23 is greater than 3.0 mm, the strength of the tubular portion 20 does not become too low, and the trocar tube is easy to thrust into the body wall, though it depends on the material used. If smaller than 50 mm, the outer diameter of the rear end 21 of the tubular porton 20 does not become too large and the trocar is easy to thrust into the body wall. The number of the aforementioned strips 23 is within 4 to 50, preferably 6 to 12, and especially preferably 6 to 8.

There is no special limitation on the material for the elastic outer tube 24 except that the material has the needed elasticity, airtightness, and durability. Silicone rubber, latex rubber, polyurethane, and copolymer of ethylene and vinyl acetate can be enumerated for example, and silicone rubber is especially preferable.

The wall thickness of the outer tube 24 is within the range of about 0.03 to 2.0 mm, preferably about 0.05 to 0.5 mm, and is especially preferably about 0.2 mm, though it depends on the material used and the diameter of the tubular portion 20. If the wall thickness of the outer tube 24 is smaller than 0.03 mm, the outer tube 24 can tear when a device is inserted through the tubular portion 20. If smaller than 2.0 mm, the trocar is easy to thrust into the body wall.

The inner diameter of the rear end 21 of the tubular portion 20 is within the range of about 4.0 to 50 mm, preferably about 4.5 to 30 mm, and especially preferably about 5.0 to 10 mm, though it depends on the outside diameter of the devices used. If the inner diameter of the rear end 21 is smaller than 4.0 mm, the kinds of usable operative devices are limited. If smaller than 50 mm, the trocar is easy to thrust into the body wall.

The inner diameter of the front end 22 of the tubular portion 20 is equal to or greater than about 1.0 mm, preferably about 1.5 mm, and is especially preferably about 2.0 mm. If the inner diameter of the front end 22 is greater than 1.0 mm, the expanding device is easily inserted into the trocar tube.

The length of the tubular portion 20 is within the range of about 30 to 250 mm, preferably 50 to 200 mm, and is especially preferably about 100 mm. If the length of the tubular portion 20 is greater than 30 mm, the trocar tube is easy able to extend through the thickened body wall. If smaller than 250 mm, the manipulation of some devices is not difficult.

Figure 2:
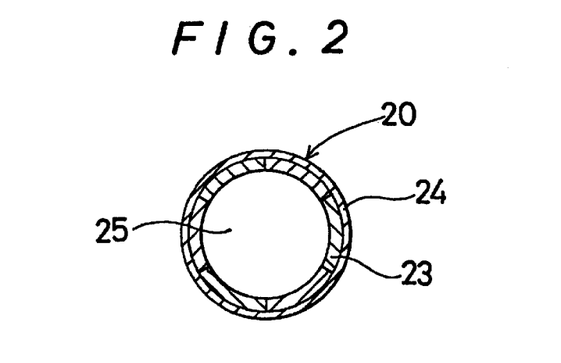
FIG. 2 is the cross-sectional view of the tube shown in FIG. 1.

FIG. 2 is the cross sectional view at a middle portion of the tubular portion of the trocar tube in FIG. 1, which shows the trocar tube in the usual state (when not expanded by the expanding device or an operative device inserted). As shown in FIG. 2, the outer tube 24 is contracted and the sides of adjacent strips 23 are in contact with each other.

The outer tube 24 keeps the lumen 25 of the tubular portion 20 airtight, and the strips 23 prevent injury from bei inflicted on the body wall.

Figure 3:
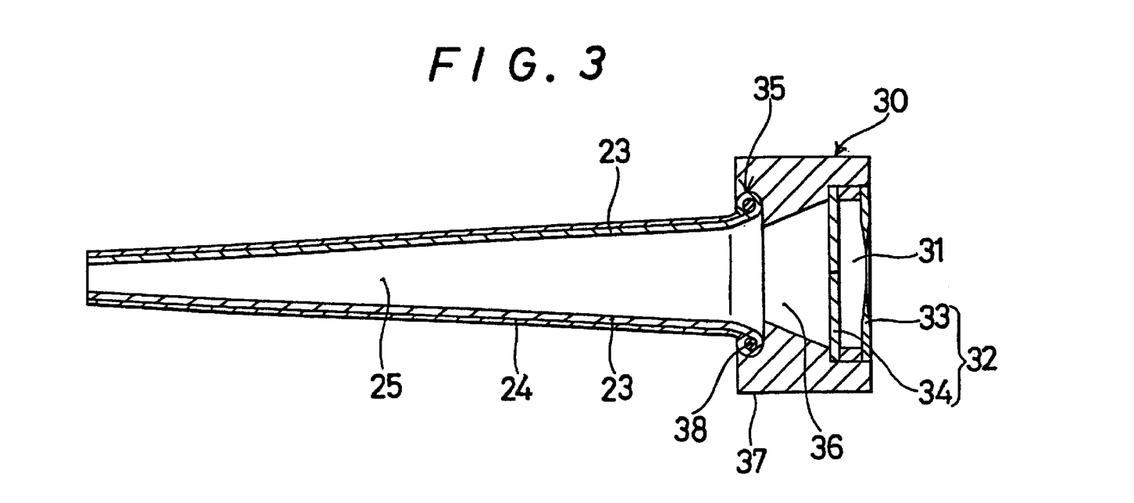
FIG. 3 is a longitudinal sectional view along the axis of the trocar tube shown in FIG. 1.

FIG. 3 is the longitudinal sectional view along the axis of the trocar tube shown in FIG. 1. As shown in FIG. 3, the grip 30 comprises an insertion opening 31 from which the expanding device (or an operative device) is inserted, a valve 32 for retaining airtightness to maintain the pressure of the gas injected in the abdominal cavity, a tubular portion connecting part 35 for holding the rear end 21 of the tubular portion 20, and an opening 36 which communicates with the lumen 25 of the tubular portion 20.

The valve 32 comprises a slit valve member 34 provided with a slit which closes to retain airtightness when the expanding device described later (or an operative device) is not inserted and expands to permit the insertion of the expanding device (or an operative device) when the expanding device (or an operative device) is inserted in the trocar tube 10, and a sealing member 33 for sealing the gap between the inside surce of the insertion opening 31 and the expanding device (or an device) when the expanding device (or an device) is inserted in the trocar tube 10.

The tubular portion-connecting part 35 comprises a holding ring 38. The rear ends of the strips 23 are wound on the holding ring 38 to hold the strips 23 so that their front ends can move in the radial direction but cannot move in the circumferential direction.

The rear end of the outer tube 24 of the tubular portion 20 is bonded to the body 37 of the grip 30 in the airtight fashion.

The diameter of the insertion opening 31 is preferably within the range of 1.0 to 50 mm, especially preferably 1.5 to 30 mm, though it depends on the inside diameter of the tubular portion 20 and the material of the seal 33. If the diameter of the insertion opening 31 is greater than 1.0 mm, many kinds of usable operative devices can be used. If smaller than 50 mm, the inside diameter of the tubular portion 20 dose not become too large.

For the material for the body 37 of the grip 30, metallic materials such as stainless steel and an aluminum alloy and synthetic resins such as polyamide, poly(vinyl chloride), polycarbonate, ABS, polyethylene, polypropylene, fluorocarbon resin and acrylic resin, for example, are preferable, and polycarbonate is especially preferable.

For the material for the seal member 33 of the valve 32, materials with an elasticity such as silicone rubber, latex rubber, polyurethane, and copolymer of ethylene and vinyl acetate are preferable. Silicone rubber is especially preferable.

The thickness of the seal member 33 is within the range of about 0.03 to 2.0 mm, preferably about 0.05 to 0.5 mm, and is especially preferably about 0.3 mm. If the thickness of the seal member 33 is greater than 0.03 mm, the seal member 33 may not tear when the expanding device is inserted. If smaller than 2.0 mm, the insertion of the expanding device is easy.

For the material for the slit valve 34 of the valve 32, materials with an elasticity such as silicone rubber, latex rubber, polyurethane, and copolymer of ethylene and vinyl acetate are preferable, and silicone rubber is especially preferable, as for the material for the seal 33.

The thickness of the slit valve 34 is within the range of about 0.1 to 3.0 mm, preferably about 0.2 to 2.0 mm, and is especially preferably about 1.0 mm. If the thickness of the slit valve 34 is greater than 0.1 mm, the strength of the slit valve 34 is not too low to withstand the pressure of the gas, and the valve 34 can not tear when the expanding device (or an operative device) is inserted. If smaller than 3.0 mm, the insertion of the expanding device (or an operative device) is easy.

Figure 4:
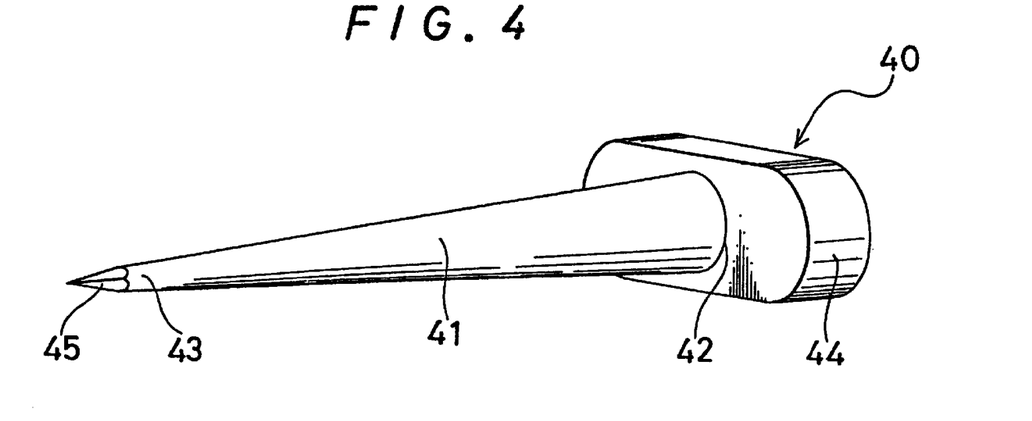
FIG. 4 is a perspective view of an embodiment of a trocar needle of this invention.

FIG. 4 is a perspective view of an embodiment of the trocar needle (blade) of this invention. As shown in the Figure, the trocar needle 40 comprises a shaft 41, a grip 44 attached to the rear end 42 of the shaft 41, and a piercing end 45 formed at the front end portion 43 of the shaft 41.

When the trocar needle 40 is inserted from the insertion opening 31 of the grip 30 in the lumen 25 of the trocar tube 10, the piercing end 45 of the trocar needle 40 projects from the front end 22 of the tubular portion 20 of the trocar tube 10. In this state, the trocar tube 10 is thrust into the abdominal cavity by piercing the body wall with the piercing end 45 of the trocar needle 40, and the trocar needle 45 alone is pulled out, leaving the trocar tube 10. Then, the expanding device 50 is pushed into the trocar tube 10 thus left, and operative devices such as an endoscope, forceps, and electric cautery are inserted into the abdominal cavity through the expanding device 50.

Since there is a possibility that the trocar needle 40 alone pierces into the abdominal cavity and the tubular portion 20 of the trocar tube 10 collapses in the direction of the axis without thrusting through the body wall, the trocar needle 40 is preferably made in the form fitting in the lumen of the trocar tube 10 in the usual state. It is especially preferable that the front end portion 43 of the shaft 41 is in contact with the inside surfae of the front end 22 of the trocar tube 10.

Although the shaft 41 of the trocar needle 40 of the embodiment shown in FIG. 4 is substantially of a cone which becomes gradually smaller in diameter from the rear end to the front end, it may be of any other form such as a pyramid or a form resembling a pyramid except that the material has a strength able to withstand the resistance when the trocar is thrust into the body wall. It is preferable that the shaft 41 has a form approximately similar to the form of the lumen 25 of the tubular portion 20 of the trocar tube 10 in the usual state.

For the material fnr the shaft 41, metallic materials such as stainless steel, an aluminum alloy, super high-resilience alloy and shape-memory alloy, and synthetic resins such as polycarbonate, acrylic resin, ABS, polypropylene, polyethylene, fluorocarbon resin, PEK(polyether keton) and PEEK(polyethyl ether keton) are preferable, and stainless steel is especially preferable.

The overall length of the shaft 41 is within the range of about 40 to 300 mm, preferably about 60 to 250 mm, and is especially preferably about 150 mm. If the length of the shaft 41 is smaller than 40 mm, the piercing end 45 does not project from the front end of the trocar tube 10. If greater than 300 mm, the trocar needle 40 can pierce too deep into the abdominal cavity and inflict injury on the organs in the abdomen.

The outside diameter of the rear end 42 of the shaft 41 is determined so as to be suited to the inside diameter of the rear end 21 of the trocar tube 10. It is within the range of about 5.0 to 50 mm, preferably about 6.0 to 30 mm, and is especially preferably about 7.5 mm.

The outside diameter of the front end 43 of the shaft 41 is determined so as to suited to the inside diameter of the front end 22 of the trocar tube 10. It is within the range of about 1.0 to 15 mm, preferably about 2.0 to 10 mm, and is especially preferably about 2.0 mm.

For the material for the grip 44, metallic materials such as stainless steel and an aluminum alloy, and synthetic resins such as polyamide, poly(vinyl chloride), polycarbonate, ABS, polyethylene, polypropylene, fluorocarbon resin and acrylic resin, for example, are preferable, and polycarbonate is especially preferable.

Figure 5:
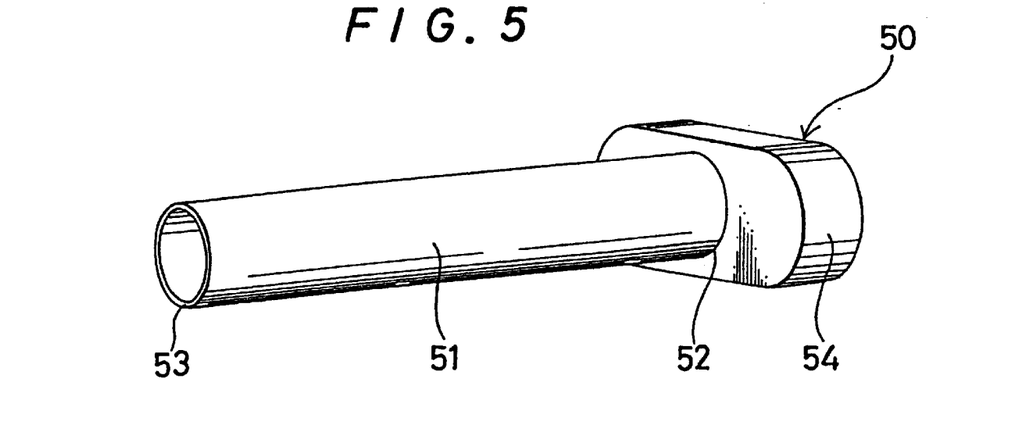
FIG. 5 is a perspective view of an expanding device for expanding the the tube of this invention.

FIG. 5 is a perspective view of the expanding device for expanding the trocar tube of this invention. As shown in the Figure, the expanding device 50 comprises a tubular member 51 (second tubular portion) for allowing the insertion of operative devices into the abdominal cavity and a grip (grip member) 54 attached to the rear end 52 of the tubular member 51. The expanding device 50 of an inside diameter suited to the outside diameter of the operative device used is inserted fom the insertion opening 31 of the grip 30 of the aforementioned t tube 10 into the lumen 25 to expand the tubular portion 20 of the trocar tube 10.

Therefore, a plurality of the expanding devices 50 of different inside diameters are prepared or use beforehand, and one of those expanding devices 50 suited to the operative device used is inserted into the trocar tube 10 to expand the front end 22 of the tubular portion 20 and the operative device is inserted into the abdominal cavity through the expanding device 50. Some conventional trocar tubes (cannula) may also be used instead of the expanding device. An operative device whose functioning parts (cutting or clamping parts, for example) and shafts are made of a rigid material and have an almost uniform outside diameter, such as a clipping forceps, can be inserted without using the expanding device 50 and expand the front end 22 of the trocar tube 10. However, when usig an operative device used for grasping and taking out the organ such as the gallbladder or part of an organ excised by the surgery, such as a grasping forceps, a pass of a uniform inside diameter is necessary to pull out the device, and therefore it is preferable to use the expanding device 50.

For the material for the tubular member 51 of the expanding device 50, metallic materials such as stainless steel an aluminum alloy, a super high-resilience metal and a shape-memory alloy, and synthetic resins such as polyamide, poly(vinyl chloride), polycarbonate, ABS, polyethylene, polypropylene, fluorocarbon resin and acrylic resin can be enumerated for example. The aforementioned synthetic resins which are not electrically conductive are preferable, and polycarbonate is especially preferable, taking into account the use of electric devices such as an electric cautery.

The overall length of the tubular member 51 of the expanding device 50 is within the range of about 40 to 300 mm, preferably about 60 to 250 mm, and is especially preferably about 130 mm. If the length of the tubular member 51 is smaller than 40 mm, the tubular member 51 may not extend through the thickened body wall. If greater than 300 mm, the manipulation of the device inserted through the expanding device is difficult.

The inside diameter of the tubular member 51 of the expanding device 50 is within the range of about 2.0 to 49 mm, preferably about 3.0 to 30 mm, and especially preferably about 3.0 to 20 mm, though it depends on the outside diameter of the operative device used. If the inside diameter of the tubular member 51 is greater than 3.0 mm, many kinds of usable operative devices can be used. If smaller than 49 mm, the trocar dose not become too invasive. The wall thickness of the tubular member 51 of the expanding device 50 is within the range of about 0.05 to 20 mm, preferably about 0.1 to 1.5 mm, and is especially preferably about 1.0 mm, though it depends on the operative device used.

The outside diameter of the tubular member 51 of the expanding device 50 is within the range of about 3.0 to 50 mm, preferably about 3.0 to 31 mm, and especially preferably about 3.0 to 21 mm, though it depends on the wall thickness of the tubular member 51 and the outside diameter of the operative device used.

Figure 6:
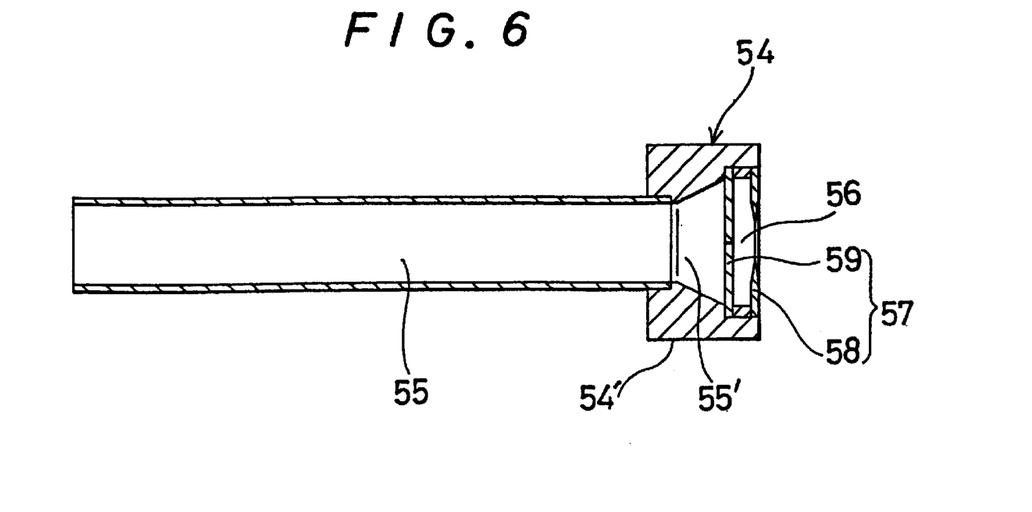
FIG. 6 is a longitudinal sectional view along the axis of the expanding device shown in FIG. 5.

FIG. 6 is the longitudinal sectional view along the axis of the expanding device shown in FIG. 5. As shown in the Figure, the grip member 54 comprises an insertion opening 56 from which an operative device is inserted, a valve 57 for retaining airtightness to maintain the pressure of the gas injected in the abdominal cavity, and an opening 55' which communicates with the lumen 55 of the tubular member 51.

For the material or the body 54' of the grip 54, metallic materials such as stainless steel and an aluminum alloy, and synthetic resins such as polyamide, poly(vinyl chloride), polycarbonate, ABS, polyethylene, polypropylene, fluorocarbon resin, for example, are preferable, and polycarbonate is especially preferable.

The valve 57 comprises a slit valve 59 provided with a slit which closes to retain airightness when a device is not inserted and expands to permit the insertion of a device when a device is inserted, and a seal 58 for sealing the gap between the inside surface of the insertion opening 56 and the inserted device when a device is inserted.

For the material for the seal 58 of the valve 57, materials with an elasticity such as silicone rubber latex rubber, polyurethane, and copolymer of ethylene and vinyl acetate are preferable, and silicone rubber is especially preferable, as for the material for the seal 33 of the trocar tube 10.

The thickness of the seal 58 is within the range of about 0.03 to 2.0 mm, preferably about 0.05 to 0.5 mm, and is especially preferably about 0.3 mm, as the thickness of the seal 33 of the trocar tube 10. If the thickness of the seal 58 is greater than 0.03 mm, the seal 58 may not tear when an operative device is inserted. If smaller than 2.0 mm, the insertion of a device is easy.

For the material for the slit valve 59 of the valve 57, materials with an elasticity such as silicone rubber, latex rubber, polyurethane, and copolymer of ethylene and vinyl acetate are preferable, and silicone rubber is especially preferable, as for the material for the seal 57.

Figure 7:
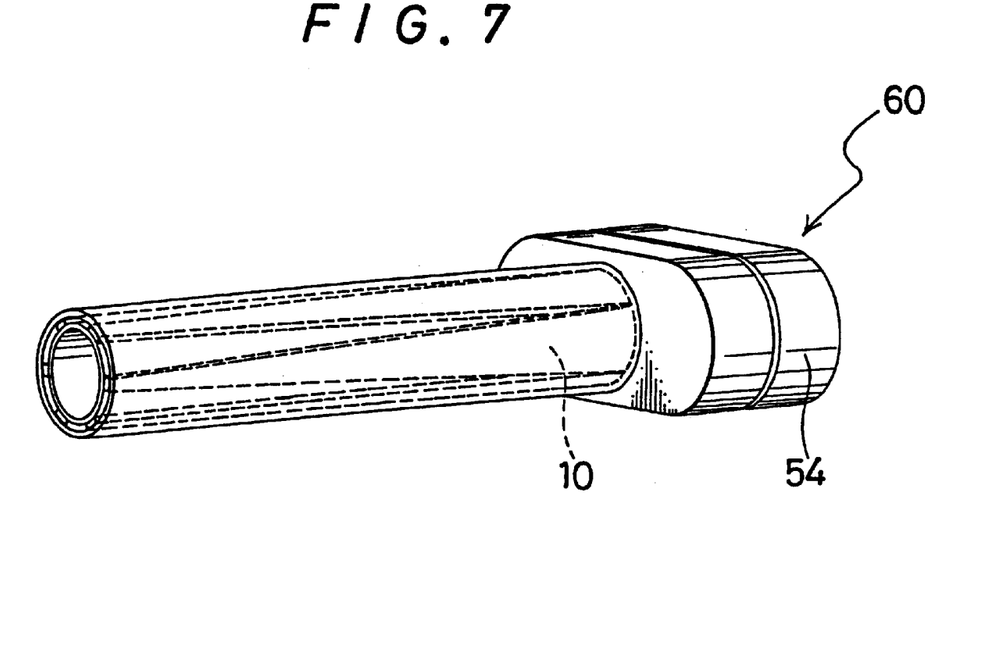
FIG. 7 is a perspective view showing the state in which the expanding device is inserted in the trocar tube of the embodoiment shown in FIG. 1.
Figure 8:
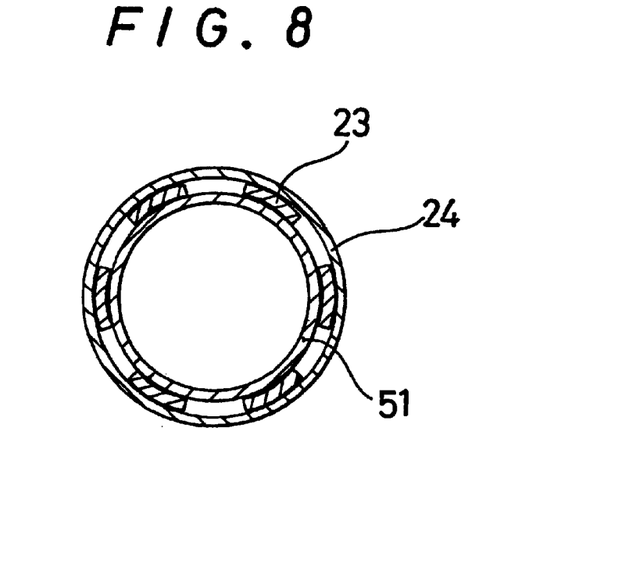
FIG. 8 is the cross-sectional view of FIG. 7 showing the state in which the expanding device is inserted in the trocar tube of the embodiment shown in FIG. 1.

The thickness of the slit valve 59 is within the range of about 0.1 to 3.0 mm, preferably about 0.2 to 2.0 mm, and is especially preferably about 1.0 mm. If the thickness of the slit valve 59 is smaller than 0.1 mm, the strength of the valve 59 is too low to withstand the pressure of the gas, and the slit valve 59 can tear when an operative device is inserted. If greater an 3.0 mm, the insertion of a device is difficult. FIG. 7 is a perspective view showing the state in which the expanding device is inserted in the trocar tube of this invention. FIG. 8 is the cross-sectional view at a middle portion of the trocar shown in FIG. 7. The trocar 60 of this invention comprises the trocar tube 10 shown in FIG. 1 and the trocar needle 40 shown in FIG. 4. As shown in FIG. 7, the trocar 60 of this invention may also comprise the expanding device 50 shown in FIG. 5. When the expanding device 50 is inserted in the trocar tube 10, the outer tube 24 is expanded radially and the gaps between adjacent strips 23 are widened as shown in FIGS. 7 and 8.

When the trocar 60 of this invention is used, first the trocar needle 40 is inserted into the trocar tube 10, and the piercing end 45 of the trocar needle 40 projects from the front end 22 of the trocar tube 10. The trocar 60 is then thrust into the abdominal cavity by piercing through the body wall with the piercing end 45 of the trocar needle 40, and the trocar needle 40 alone is pulled out leaving the trocar tube 10. Next, the expanding device 50 is inserted into the trocar tube 10 to expand the front end 22 of the trocar tube 10. In this state, operative devices such as an endoscope, forceps, and electric cautery are inserted into the abdominal cavity through the expanding device 50.

Since the tubular portion 20 of the trocar tube 10 is of a cone the front end of which is smaller than the rear end in diameter (the usual state), and the shape of the shaft 41 of the trocar needle 40 is closely similar to that of the lumen 25 of the trocar tube 10, the trocar of this invention 60 can be thrust into the abdominal cavity by making only a small puncture in the body wall and expanding it. Further, since only the front end side of the trocar tube 10 is expanded by the insertion of the expanding device 20, the excoriation left in the body wall is smaller than that left by a conventional trocar. In addition, since the resistance to the thrust is small the possibility of hurting the organs in the abdominal cavity by accident is eliminated.

Further, the manipulation of the operative device inserted through the trocar tube 10 is made easier by using the expanding device 50 suited to the diameter of the operative device used, and surgery can be performed safely. When an operative device of a different diameter must be used, the expanding device used can be replaced with another expanding device suited to the diameter of the device, and therefore there is not need to stab another trocar in the abdominal cavity during the operation.

Next, another embodiment of the trocar needle of this invention and the trocar equipped with the trocar needle are described below.

Figure 9:
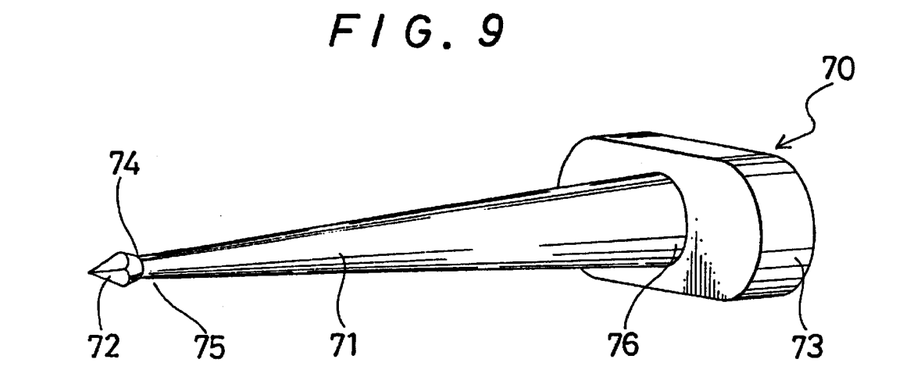
FIG. 9 is a perspective view of an embodiment of the trocar needle of this invention.

FIG. 9 is a perspective view of another embodiment of the trocar needle of this invention.

In FIG. 9, the trocar needle 70 of this invention comprises a shaft 71, a piercing end 72 formed at the front end of the shaft 71, and a grip 73 attached to the rear end of the shaft 71. The shaft 71 is substantially of a cone which becomes gradually smaller in diameter toward the front end, and has a neck at the rear of the piercing end 72. The neck is formed by the tapered portion 74 which becomes gradually larger in diameter to the piercing end and the front end portion 75 of the shaft 71 at the rear of the tapered portion 74.

Figure 10:
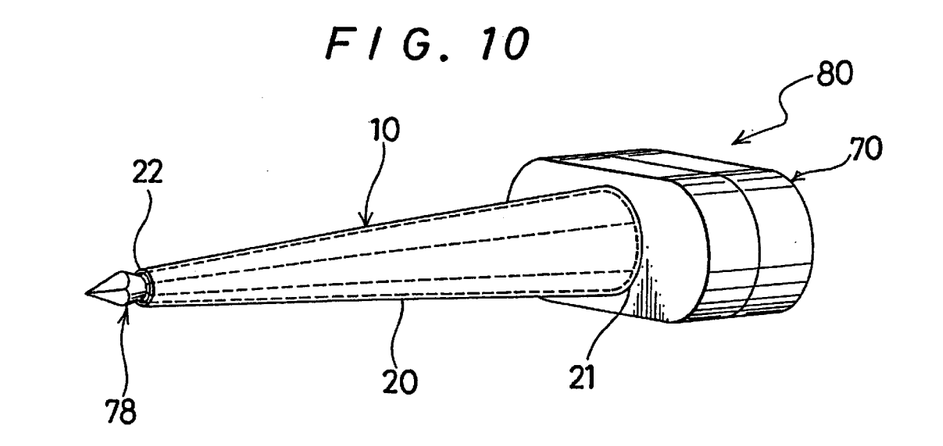
FIG. 10 is a perspective view of the trocar which is equipped with the trocar needle of the embodiment shown in FIG. 9 and the trocar tube shown in FIG. 1.

The piercing end 72 becomes gradually smaller in diameter toward the front end, and the front end is sharply pointed. The trocar needle 70 is inserted into the trocar tube, expanding the front end portion of the trocar tube by the piercing end 72. The trocar needle 70 is made so that the head 78 consisting of the piercing end 72 and the tapered portion 74 projects from the front end of the trocar tube and that the front end of the trocar tube extends up to just behind the tapered portion 74, as shown in FIG. 10. The front end of the trocar tube is thereby supported by the tapered portion 74 and the front end portion 75 of the shaft 71. The trocar is thrust through the body wall in this state, and hence the front end of the trocar tube does not catch on the body wall. The trocar needle 70 can be pulled out of the trocar tube smoothly by slowly pulling out the trocar needle and thereby expanding the front end of the trocar tube by the tapered portion 74.

Although the shaft 71 of the trocar needle 70 shown in FIG. 9 is substantially of a cone which becomes gradually smaller in diameter toward the front end, it may be of any other form such as a pyramid or a form resembling a pyramid. The shaft 71 is preferably of a form suited to the lumen of the trocar tube, especially a form such that the almost entire surface comes into contact with the inside surface of the tubular portion of the trocar tube in the usual state.

There is no special limitation on the material for the shaft 71 except that the material has a strength able to withstand the resistance when the trocar is thrust into the body wall. Metallic materials such as stainless steel, an aluminum alloy, super high-resilience alloy and shape-memory alloy, and synthetic resins such as polycarbonate, acrylic resin, ABS, polypropylene, polyethylene, fluorocarbon resin, PEK and PEEK are preferable, and stainless steel is especially preferable.

The overall length of the shaft 71 is within the range of about 40 to 300 mm, preferably about 60 to 250 mm, and is especially preferably about 140 mm. If the length of the shaft 71 is smaller than 40 mm, the trocar needle 70 may not pierce through the thickened body wall. If greater than 300 mm, the trocar needle 70 can pierce too deep into the abdominal cavity and inflict injury on the organs in the abdomen.

The outside diameter of the rear end 76 of the shaft 71 is determined so as to be suited to the inside diameter of the rear end of the trocar tube. It is within the range of about 5.0 to 50 nm, preferably about 6.0 to 30 mm, and is especially preferably about 7.5 mm. If the outside diameter of the rear end 76 is smaller than 5.0 mm, the corresponding inside diameter of the rear end of the trocar tube becomes too small and the kinds of usable operative devices are limited. If greater than 50 mm, the trocar becomes too invasive and the wound needs a long time to heal.

The outside diameter of the front end 75 of the shaft 71 is determined so as to be suited to the inside diameter of the front end of the trocar tube. It is within the range of about 1.0 to 15 mm, preferably about 1.5 to 10 mm, and is especially preferably about 2.0 mm. If the outside diameter of the front end 75 is smaller than 1.0 mm, the aforementioned expanding device may not be able to be inserted. If greater than 15 mm, the diameter of the piercing end becomes too large in order to form a smaller diameter portion for supporting the front end of the trocar tube.

For the material for the grip 73, metallic materials such as stainless steel and an aluminum alloy, and synthetic resins such as polyamide, poly(vinyl chloride), polycarbonate, ABS, polyethylene, polypropylene, fluorocarbon resin and acrylic resin, for example, are preferable, and stainless steel especially preferable.

The head 78 is preferably made as a single part together with the shaft 71, but may be made separately from the shaft 71 and joined to the front end of the shaft 71.

For the material for the head 78, metallic materials such as stainless steel, an aluminum alloy, super high-resilience alloy and shape-memory alloy, and synthetic resins such as polycarbonate, acrylic resin, ABS, polypropylene, polyethylene, fluorocarbon resin, PEK and PEEK are preferable, and stainless steel is especially preferable, as for the material for the shaft 71.

The outside diameter of the head 74 at the part between the piercing end 72 and the tapered portion is within the range of about 1.05 to 18 mm, preferably about 2.1 to 11.5 mm, and is especially preferably about 3.5 mm, though it depends on the wall thickness of the tubular portion of the trocar tube. If the outside diameter of this part of the head 74 is greater than 1.05 mm, it is easy to support the front end of the trocar tube. If smaller than 18 mm, the trocar needle 70 is easy to pull out of the trocar tube.

The overall length of the head 78 is within the range of about 2.0 to 30 mm, preferably about 3.0 to 20 mm, and is especially preferably about 10 mm. If the length of the head 78 is smaller than 2.0 mm, the thrust into the body wall becomes difficult because of the increased resistance. If smaller than 30 mm, the trocar needle 70 can not pierce too deep into the abdominal cavity.

Figure 11:
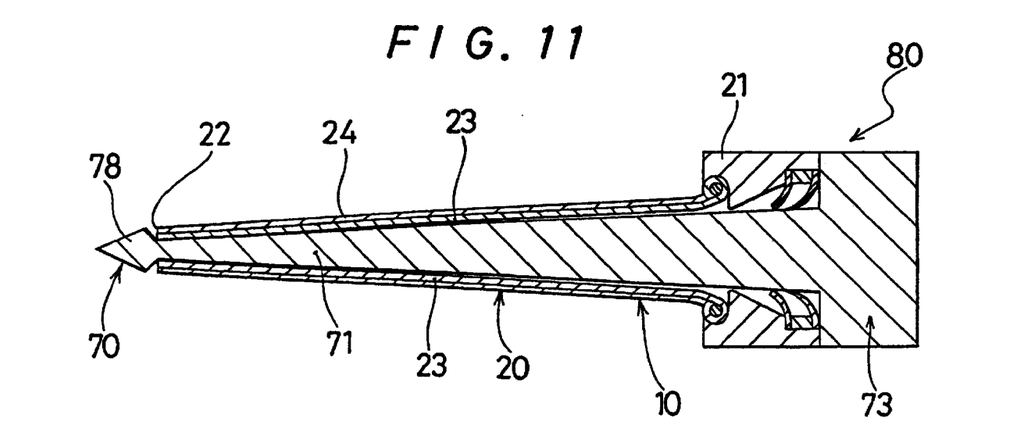
FIG. 11 is a longitudinal sectional view along the axis of the trocar shown in FIG. 9.

Next, the trocar equipped with the trocar needle of this embodiment is described below using FIGS. 10 and 11. FIG. 10 is a perspective view of the trocar equipped with the trocar needle of the embodiment shown in FIG. 9. FIG. 11 is a longitudinal sectional view along the axis of the trocar equipped with the trocar needle of the embodiment shown in FIG. 9.

As shown in FIGS. 10 and 11, the trocar 80 comprises the above trocar needle 70 and the trocar tube 10 which has the lumen of almost the same form as the shaft 71 of the trocar needle 70. The trocar needle 70 is inserted in the lumen of the trocar tube 10, and in this state the trocar needle and the trocar tube are thrust into the body wall. For the trocar tube of this embodiment, the trocar tube 10 described above (the one shown in FIG. 1) is used.

The tubular portion 20 of the trocar tube 10 is formed so that the front end 22 can expand to a larger diameter when the trocar needle 70 or an operative device is inserted and pulled out. When the trocar needle 70 is inserted, the front end 22 of the tubular portion 20 is expanded by the piercing end of the trocar needle 70 pushed into the lumen. When the trocar needle 70 is pulled out, the front end 22 is expanded from outside the tubular portion 20 by the tapered portion 74 of the trocar needle 70. To insert an operative device, it is preferable to expand the front end of the tubular portion 20 beforehand by inserting the aforementioned expanding device into the lumen of the trocar tube 10, though some device may be inserted through the lumen of the trocar tube 10 directory without the expanding device.

When the trocar needle 70 is inserted in the trocar tube 10, the head 78 of the trocar needle 70 projects from the front end of the trocar tube 10, and the front end of the trocar tube 10 is at or just behind the tapered portion 74. Therefore, the front end of the trocar tube 10 is supported by the small-diameter portion behind the head 78 of the shaft 71 and hence does not catch on the body wall when the trocar 80 is thrust into the body wall. When the trocar needle 70 is pulled out, the front end 22 of the trocar tube 10 can be expanded by the tapered portion 74 by gradually pulling out the trocar needle 70, and hence the trocar needle 70 can be smoothly pulled out of the trocar tube 10.

Next, the trocar tube which forms the trocar equipped with the trocar needle of this invention is described below.

As shown in FIG. 11, the trocar tube 10 comprises a tubular portion 20 and a grip 30 attached to the rear end of the tubular portion 20. The tubular portion 20 is made so that it becomes gradually smaller in diameter from the rear end to the front end when thrust into the body wall and so that the front end can be expanded when the trocar needle 70 is inserted into and pulled out of the trocar tube 10 and when the expanding device (or an operative device) is inserted into the abdominal cavity through the trocar tube 10.

When the trocar needle 70 is inserted into the trocar tube 10, the front end 22 of the trocar tube 10 is expanded by the piercing end 72 of the trocar needle 70. When the trocar needle 70 is pulled out, the front end 22 of the trocar tube 10 is expanded by the tapered portion 74 of the trocar needle 70. To insert an operative device, it is preferable to expand the tubular portion 20 beforehand by inserting the expanding device into the trocar tube 10, though the front end 22 of the trocar tube 10 can be expanded without using the expanding device when an operative device whose functioning parts (cutting or clamping parts, for example) and shafts are made of a rigid material and have an almost uniform outside diameter such as a clipping forceps is inserted.

The tubular portion 20 comprises a plurality of strips 23 which are arranged in a ring and a outer tube 24 which covers the outside surface of the strips. The strips 23 are of a trapezoid the width of the front end of which is smaller than that of the rear end. The outer tube 24 has an elasticity and thereby prevents injury from being inflicted on the body wall when the trocar tube 10 is thrust into the abdominal cavity and retains airtightness. When the trocar needle 70 is fitted in the trocar tube 10, the outer tube 24 is contracted and the sides of the stips 23 are in contact with each other.

There is no special limitation on the material for the strips 23 except that the material has a strength able to withstand the force which the tubular portion 20 receives when the front end of the tubular portion 20 catches on the body wall and the pressure from the body wall. Metallic materials such as stainless steel, an aluminum alloy, a super high-resilience metal and a shape-memory alloy and synthetic resins such as polyamide, poly(vinyl chloride), polycarbonate, ABS, polyethylene, polypropylene, fluorocarbon resin and acrylic resin can be enumerated for example. The aforementioned synthetic resins which are not electrically conductive are preferable, and polycarbonate and ABS are specially preferable, talkng into account the use of electric devices such as an electric cautery.

The thickness of the strips 23 is within the range of about 0.05 to 3.0 mm, preferably about 0.1 to 1.5 mm, and is especially preferably about 0.5 mm, though it depends on the material used. If the thickness of the strips 23 is smaller than 0.05 mm, the trocar tube may not be able to withstand the pressure of the body wall, and if greater than 3.0 mm, the trocar is difficult to thrust into the body wall because of the increased resistance.

The width of the front end of the strips 23 depends on the number of the strips 23 forming the tubular portion 20. When the number of the strips 23 is six, for example, the width of the front end is equal to or smaller than about 6.0 mm, preferably about 4.0 mm, and is especially preferably about 1.5 mm. If the width of the front end is greater than 6.0 mm, the inside and outside diameters of the front end 22 of the tubular portion 20 becomes too large and the trocar is difficult to thrust into the body wall because of the increased resistance.

The width of the rear end of the strips 23 also depends on the number of the strips 23 forming the tubular portion 20. When the number of the strips 23 is six, for example, the width of the rear end is equal to or smaller than about 3.0 to 50 mm, preferably about 5.0 to 20 mm, and is especially preferable about 6.0 mm. If the width of the rear end is smaller than 3.0 mm, the strength of the tubular portion 20 becomes too low, and the tubular portion 20 can deform or collapse when the trocar is thrust into the body wall making the thrusting difficult, though the width depends on the material used. If the width of the rear end of the strips 23 is greater than 50 mm, the outer diameter of the rear end 21 of the tubular portion 20 becomes too large and the trocar is difficult to thrust into the body wall because of the increased resistance to the thrust.

The number of the aforementioned strips 23 is within 4 to 50, preferably 6 to 12, and is especially preferably about 6.

There is no special limitation on the material for the outer tube 24 except that the material has the needed elasticity, airtightness, and durability. Silicone rubber, latex rubber, polyurethane, and copolymer of ethylene and vinyl acetate can be enumerated for example, and silicone rubber is especially preferable.

The wall thickness of the outer tube 24 is within the range of about 0.03 to 2.0 mm, preferably about 0.05 to 0.5 mm, and is especially preferably about 0.2 mm, though it depends on the material used and the diameter of the tubular. portion 20. If the wall thickness of the outer tube 24 is smaller than 0.03 mm, the outer tube 24 can tear when a device is inserted through the tubular portion 20. If greater than 2.0 mm, the trocar is difficult to thrust into the body wall because of the increased resistance to the thrust The inner diameter of the rear end 21 of the tubular portion 20 is within the range of about 40 to 50 mm, preferably about 4.5 to 30 mm, and epecially preferably about 5.0 to 10 mm, though it depends on the outside diameter of the devices used. If the inner diameter of the rear end 21 is smaller than 4.0 mm, the kinds of usable operative devices are limited. If greater than 50 mm, the trocar becomes too invasive and the wound needs a long time to heal The inner diameter of the front end 22 of the tubular portion 20 is equal to or greater than about 1.0 mm, preferably about 2.0 mm, and about 2.5 mm is especially preferable. If the inner diameter of the front end 22 is less than 1.0 mm, the expanding device may not be able to be inserted into the trocar tube.

The length of the tubular portion 20 is within the range of about 30 to 250 mm, preferably 50 to 200 mm, and is especially preferably about 100 mm. If the length of the tubular portion 20 is less than 30 mm, the trocar tube may not be able to extend through the thickened body wall. If greater than 250 mm, the manipulation of some devices is difficult.

The grip 30 comprises an insertion opening 31 from which the expanding device (or an operative device) is inserted, a valve 32 for retaining airtightness to maintain the pressure of the gas injected in the abdominal cavity, a tubular portion-connecting part 35 for holding the rear end 21 of the tubular portion 20, and an opening 36 which communicates with the lumen 25 of the tubular portion 20, as shown in FIG. 3.

The valve 32 comprises a slit valve 34 provided with a slit which closes to retain airtightness when the expanding device (or an operative device) is not inserted and expands to permit the insertion of the expanding device (or an operative device) when the expanding device (or an operative device) is inserted into the trocar tube 10, and a seal 33 for sealing the gap between the inside surface of the insertion opening 31 and the expanding device (or an device) when the expanding device (or an device) is inserted in the trocar tube 10.

The tubular portion-connecting part 35 comprises a holding ring 38. The rear ends of the strips 23 are wound on the holding ring 38 to hold the strips 23 so that their front ends can move in the radial direction but cannot move in the circumferential direction.

The rear end of the outer tube 24 of the tubular portion 20 is bonded to the body 37 of the grip 30 in the airtight fashion.

The diameter of the insertion opening 31 is preferably within the range of 1.0 to 50 mm, especially preferably 1.5 to 30 mm, though it depends on the inside diameter of the tubular portion 20 and the material of the valve 32. If the diameter of the insertion opening 31 is smaller than 1.0 mm, the kinds of usable operative devices are limited. If greater than 50 mm, the inside diameter of the tubular portion 20 also becomes large, and hence the trocar becomes too invasive and the wound needs a long time to heal.

For the material for the body 37 of the grip 30, metallic materials such as stainless steel and an aluminum alloy and synthetic resins such as polyamide, poly(vinyl chloride), polycarbonate, ABS, polyethylene, polypropylene, fluorocarbon resin and acrylic resin, for example, are preferable, and polycarbonate is especially preferable.

For the material for the slit valve 34 of the valve 32, materials with an elasticity such as silicone rubber, latex rubber, polyurethane, and copolymer of ethylene and vinyl acetate are preferable. Silicone rubber is especially preferable.

The thickness of the slit valve 34 is within the range of about 0.1 to 3.0 mm, preferably about 0.2 to 2.0 mm, and is especially preferably about 1.0 mm. If the thickness of the slit valve 34 is smaller than 0.1 mm, the slit valve 34 can tear when the expanding device is inserted. If greater than 3.0 mm, the insertion of the expanding device is difficult.

For the material for the seal 33 of the valve 32, materials with an elasticity such as silicone rubber, latex rubber, polyurethane, and copolymer of ethylene and vinyl acetate are preferable, and silicone rubber is especially preferable, as for the material or the slit valve 34.

The thickness of the seal 33 is within the range of about 0.01 to 2.0 mm, preferably about 0.05 to 0.5 mm, and is especially preferably about 0.3 mm. If the thickness of the seal 33 is smaller than 0.03 mm, the strength of the seal 33 is too low to withstand the pressure of the gas, and the seal 33 can tear when the expanding device is inserted. If greater than 2.0 mm, the insertion of the expanding device is difficult.

Next, the expanding device used for expanding the trocar tube of this trocar is described below.

As shown in FIGS. 5 and 6, the expanding device 50 comprises the tubular member 51 for allowing the insertion of operative devices into the abdominal cavity and the grip member 54 attached to the rear end 52 of the tubular member 51. The expanding device 50 of an inside diameter suited to the outside diameter of the operative device used is inserted from the insertion opening 31 of the grip 30 of the aforementioned lroar tube 10 into the lumen 25 to expand the tubular portion 20 of the trocar tube 10.

Therefore, a plurality of the expanding devices 50 of different inside diameters are prepared hr use beforehand, and one of those expanding devices 50 suited to the operative device used is inserted into the trocar tube 10 to expand the front end 22 of the tubular portion 20 and the operative device is inserted into the abdominal cavity through the expanding device 50. Some conventional tocar tubes (cannula) may also be used instead of the expanding device.

An operative device whose functioning parts (cutting or clamping parts, for example) and shafts are made of a rigid material and have an almost uniform outside diameter, such as a clipping forceps, can be inserted without using the expanding device 50 and expand the front end 22 of the trocar tube 10. However, when using an operative device used for grasping and taking out the organ such as the gallbladder or part of an organ excised by the surgery, such as a grasping forceps, a pass of a uniform inside diameter is necessary to pull out the device, and hence it is preferable to use the expanding device 50.

For the material for the tubular member 51 of the expanding device 50, metallic materials such as stainless steel, an aluminum alloy, a super high-resilience metal and a shape-memory alloy, and synthetic resins such as polyamide, poly(vinyl chloride), polycarbonate, ABS, polyethylene, polypropylene, fluorocarbon resin and acrylic encan be enumerated for example. The aforementioned synthetic resins which are not electrically conductive are preferable, and polycarbonate is especally preferable, taking into account the use of electric devices such as an electric cautery.

The overall length of the tubular member 51 of the expanding device 50 is within the range of about 40 to 300 mm, preferably about 60 to 250 mm, and is especially preferably about 130 mm. If the length of the tubular member 51 is smaller than 40 mm, the tubular member 51 may not exend through the thickened body wall. If greater than 300 mm, the manipulation of the device inserted through the expanding device is difficult.

The inside diameter of the tubular member 51 of the expanding device 50 is within the range of about 2.0 to 49 mm, preferably about 3.0 to 30 mm, and especially preferably about 3.0 to 20 mm though it depends on the outside diameter of the operative device used. If the inside diameter of the tubular member 51 is smaller than 3.0 mm, the kinds of usable operative devices are limited. If greater than 49 mm, the trocar becomes too invasive and the wound needs a long time to heal.

The wall thickness of the tubular member 51 of the expanding device 50 is within the range of about 0.05 to 2.0 mm, preferably about 0.1 to 1.5 mm, and is especially preferably about 1.0 mm, though it depends on the operative device used.

The outside diameter of the tubular member 51 of the expanding device 50 is within the range of about 3.0 to 50 mm, preferably about 3.0 to 31 mm, and especially preferably about 3.0 to 21 mm, though it depends on the wall thickness of the tubular member 51 and the outside diameter of the operative device used. The state of the trocar tube when it is expanded by the expanding device is shown in FIGS. 7 and 8. As shown in the FIGS. 7 and 8, the expanding device 50 is inserted in the lumen 25 from the opening 31 through the opening 36. The front end 22 of the trocar tube 10 is thereby expanded to a larger dimeter. In this state, the outer tube 24 is expanded and the gaps between adjacent strips 23 are widened, as is apparent by comparison with the sectional view of the trocar tube 10 shown in FIG. 2. Instead of the trocar tube as described above whose front end portion is expandable, a flexible trocar tube whose tubular portion is made of a material with an elasticity may be used.

Next, examples of the trocar tube and trocar needle of this invention and the trocar of this invention comprising the trocar tube and trocar needle are described below.

EXAMPLE 1

The trocar tube of the structure shown in FIGS. 1 to 3 was made. The natures of this trocar tube are as follows:

[Strips]
Material: Polycarbonate
Width of front end: 1.5 mm
Width of rear end: 6.0 mm
Wall thickness: 0.5 mm
[Tube]
Material: Silicone rubber
Wall thickness: 0.2 mm
[Tubular portion]
The tubular portion is made of the above strips (6 strips) and tube.
Inside diameter of front end: 2.0 mm
Inside diameter of rear end: 7.5 mm
Outside diameter of front end: 3.0 mm
Outside diameter of rear end: 8.5 mm
Wall thickness: 0.5 mm
Overall length: 100 mm
[Body of grip]
Material: Polycarbonate[Seal]
Material: Silicone rubber
Thickness: 0.3 mm
[Slit valve]
Material: Silicone rubber
Thickness: 1.0 mm
[Shaft]
Material: SUS304
Outside diameter of front end: 2.0 mm
Outside diameter of rear end: 7.5 mm
Overall length: 140 mm
[Grip]
Material: Polycarbonate Next, the expanding devices 50 of the structure shown in FIGS. 5 and 6 were made. Three kinds of the expanding device different only in the inside and outside diameters of the tubular portion were made.

[Tubular member of the expanding device]
Material Polycarbonate
Inside diameter: 3.0 mm
Outside diameter: 4.0 mm
Wall thickness: 1.0 mm
Overall length: 130 mm
[Body of grip member]
Material: Polycarbonate
[Seal]

Material: Silicone rubber

Thickness: 0.3 mm

[Slit valve]

Material: Silicone rubber

Thickness: 1.0 mm

EXAMPLE 2

Example 2 is same as of Example 1 except the tubular member of the expanding device.

Tubular member of tihe expanding device]

Material: Same as of Example 1

Inside diameter of front end: 4.5 mm

Outside diameter: 5.5 mm

Wall thickness: 1.0 mm

Overall length: Same as of Example 1

EXAMPLE 3

Example 3 is same as of Example 1 except the tubular member of the expanding device.

[Tubular member of the expanding device]

Material: Same as of Example 1

Inside diameter of front end: 6.0 mm

Outside diameter: 7.0 mm

Wall thicness: 1.0 mm

Overall length: Same as of Example 1

EXAMPLE 4

Next, the trocar needle 70 of the form shown in FIG. 9 was made. The features of this trocar needle were as follows:

[Shaft]

Material: SUS304

Outside diameter of front end: 2.0 mm

Outside diameter of rear end: 7.5 mm

Overall length: 140 mm

[Grip]

Material: SUS304

[Head]

Material: SUS304

Overall length: 10 mm

Outside diameter: 3.5 mm Experiment

An intestine anastomosis surgery was performed using the trocar tube and the trocar needle of Example 1 and the expanding devices of Examples 1 to 3, and further the trocar needle of Example 4.

An adult mongrel dog was put under general anesthesia. Next, a gas ($CO_2$) was injected into the abdominal cavity. Then, a conventional trocar tube was inserted into the abdominal cavity using a conventional trocar. Through this trocar tube, an endoscope was inserted into the abdominal cavity, and the image taken by a miniature camera in the endoscope was displayed on a monitor screen.

Next, the trocar needle of Example 1 was inserted into the trocar tube of Example 1. The trocar needle and trocar tube, with the piercing end of the trocar needle projecting from the front end of the trocar tube, were thrust into the abdominal cavity by piercing the body wall with the piercing end. The trocar needle alone was then pulled out leaving the trocar tube in place. Next, the front end portion of the expanding device of Example 1 was inserted into the trocar tube thus left, and the entire expanding device was pushed into the trocar tube expanding the front end portion of the trocar tube by pushing the grip member.

A small spatula forceps 2.0 mmn in outside diameter was inserted into the abdominal cavity through the trocar tube of Example 1 and used.

Next, the expanding device of Example 1 was pulled out, and the expanding device of Example 2 was inserted into the trocar tube of Example 1. An electrical cautery 4.0 mm in outside diameter was inserted into the abdominal cavity through the expanding device of Example 2 and used.

Further, the expanding device of Example 2 was pulled out, and the expanding device of Example 3 was inserted into the trocar tube of Example 1. A grasping forceps 5.0 mm in outside diameter, then a needle-holder of the same outside diameter was used through the expanding device of Example 3.

The trocar of this invention did not deform and become difficult to thrust because of the resistance to the thrust caused by the friction against the body wall, and could be easily thrust into the abdominal cavity. Further, the body wall was not pressed down near the organs in the abdominal cavity, and no injury was accidentally inflicted on the organs.

When the three kinds of trocar tubes of dif&&rent diameters were inserted, the air- and liquid-tightness of the trocar tube was preserved.

Since the trocar tube of a diameter suited to the operational device used could be used, operational devices of different outside diameters could be easily manipulated.

Conventionally used trocar tubes could be used for the expanding device.

Since the trocar was thrust into the body cavity by making a small puncture in the body wall and expanding it, the excoriation left in the body wall was much smaller than that left by a conventional trocar equipped with a trocar tube which permits the insertion of an operative device 5.0 mm in outside diameter.

The resistance to the thrust and the excoriation may be further smaller if the trocar tube whose wall thickness is smaller at the front end than at the rear end is used, instead of the one whose wall thickness is uniform from the rear end to the front end as used in this experiment.

Further, although the expanding device was inserted in the trocar tube and operative devices were inserted into the body cavity through the expanding device in this experiment, operative devices whose functioning parts and shafts except the operating portion are made of a rigid material and have an almost uniform outside diameter, such as a pinching forces, clipping forceps, and electric cautery, can be inserted into the body cavity through the trocar tube without using the expanding device.

Next, the trocar needle of Example 4 was inserted into the trocar tube of Example 1, and the trocar tube and trocar needle were thrust into the abdominal cavity, and the trocar tube was put through the body wall. Then, the expanding device of Example 1 was inserted into this trocar tube to expand. Through this expanding device, a spatula forceps 2.5 mm in outside diameter was inserted into the abdominal cavity and used. Next, this expanding device of Example 1 was pulled out and the expanding device of Example 2 was inserted in the trocar tube. Through this expanding device, an electric cautery 4.0 mm in outside diameter was inserted into the body cavity and used. In the similar manner, the expanding device of Example 3 was inserted in the trocar tube, and through the expanding device a grasping forceps 5.0 mm in outside diameter and a needle-holder of the same outside diameter were inserted in the abdominal cavity and used.

The resistance to the thrust into the body wall of the trocar equipped with the trocar needle of Eample 4 was small and the trocar could be easily thrust through the body wall, as compared with the conventional trocar used for inserting the flexible endoscope into the abdominal cavity.

The force the front end of the trocar tube exerts on the body wall when the front end caught on the body wall was small, and the body wall was not pressed down near the organs in the abdominal cavity. As a result, no injury was accidentally inflicted on the organs.

The trocar was less invasive than the conventional trocar because of the decreased resistance to the thrust.

The trocar needle was easily pulled out of the trocar tube by gradually pulling out because of the tapered portion which was made in the trocar needle so as to expand front end of the trocar tube. No injury was iflicted on the body wall when the trocar needle was pulled out As described above, the trocar tube of this invention comprises a tubular portion and a grip attached to the rear end of the tubular portion, and is characterized by that the tubular portion is smaller in outside diameter at the front end than at the rear end in the usual state, and the front end portion of the tubular portion can be expanded when an operative device is inserted into the body cavity through the trocar tube. By this structure, the trocar tube of this invention permits the insertion of various kinds of operative devices of different diameters, being of low invasion which does not leave a large excoriation.

The trocar tube of this invention is characterizd by that the tubular portion comprises a plurality of strips held in a ring and an elastic tube which covers at least the outside surface of the strips. This structure of the tubular portion makes the trocar tube of this invention air- and liquid-tight, and prevents the trocar tube from inflicting injury on the body wall.

The trocar tube of this invention is characterized by that the strips are of a trapezoid the width of the front end of which is smaller than that of the rear end, hence the tubular portion being smaller in inside diameter at the front end than at the rear end. This structure reduces the resistance when the trocar is thrust into the body wall, and hence accidental infliction of injury on the organs in the abdominal cavity can be prevented.

Further, the tucar tube of this invention is characterized by that, when an operative device is inserted into the body cavity, the front end portion of said trocar tube is expanded by inserting an expanding device which comprises a second tubular portion having an outside diameter greater than the inside diameter of the front end of the tubular portion of the trocar tube in the usual state and a grip member attached to the rear end of the second tubular portion. By this structure, the trocar tube of this invention permits the insertion of various kinds of operative devices.

The trocar of this inventon comprises the above trocar tube and a trocar needle which has an piercing end and is inserted into the trocar tube, and is characterized by that tubular portion of the trocar tube is smaller in outside diameter at the front end than at the rear end in the usual state, and the front end portion of the tubular portion can be expanded when an operative device is inserted into the body cavity through the trocar tube. By this structure, the trocar tube of this invention permits the insertion of various kinds of operative devices of different diameters. The trocar tube reduces the resistance to the thrust of the trocar into the body wall and the trocar equipped with the trocar tube is easy to thrust. As a result, accidental infliction of injury on the organs in the abdominal cavity is prevented. The trocar tube is less invasive and does not leave a large excoriation.

Further, the trocar of this invention is characterzed by that the trocar needle has a shaft substantially of a cone which becomes gradually smaller from the rear end to the front end and is closely similar to the form of the lumen of the trocar portion of the trocar tube in the usual state. This structure of the trocar needle reduces the resistance when the trocar is thrust into the body wall and makes the trocar easier to thrust, and prevents the trocar tube from deforming and making the thrust difficult. The trocar is less invasive and does not leave a large excoriation.

Further, the trocar of this invention is characterized by that the front end portion of the trocar tube is expanded by inserting an expanding device which comprises a second tubular portion having an outside diameter greater than the inside diameter of the tubular portion of the trocar tube in the usual state and a grip member attached to the rear end of the second tubular portion. By this structure, various kinds of operative devices can be inserted through the trocar tube.

The trocar needle of this invention comprises a shaft, a piercing end provided at the front side of the shaft, and a grip attached to the rear end of the shaft, characterized by that the shaft becomes gradually smaller in diameter toward the front end and that a neck for supporting the front end of the trocar tube is formed between the shaft and the piercing head. By this structure of the trocar needle, the trocar becomes less invasive, the force exerted by the front end of the trocar tube on the body wall when the trocar is thrust into the body wall, and the resistance to the thrust is reduced Further, the trocar needle of this invention is characterized by that the neck is tapered so that the diameter becomes gradually larger from the shaft to the piercing end. By this structure, the front end of the trocar tube can be supported by the neck when the trocar needle is inserted in the to tube. The tapered neck makes easier the extraction of the trocar needle from the trocar tube.

The trocar equipped with the trocar needle of this invention comprises the above trocar needle and a trocar tube which comprises a tubular portion and a grip attached to the rear end of the tubular portion, the tubular portion of the trocar tube becomeig gradually smaller in diameter toward the front end when the trocar is thrust into the body wall and the front end of the tubular portion being supported by the neck or the portion near the neck. By this structure, the trocar is of low invasion, the force exerted by the front end of the trocar tube on the body wall when the trocar is thrust into the body wall is reduced, and the resistance to the thrust is small.

Further, the trocar equipped with the trocar needle of this invention is characterized by that the front end portion of the trocar tube expands when the trocar needle or an operative device is inserted. By this structure, the insertion and extraction of the trocar needle into and from the trocar tube is made easy.

Further, the trocar equipped with the trocar needle of this invention is chnracterized by that, when an operative device is inserted into the body cavity, the front end portion of said trocar tube is expanded by inserting an expanding device which comprises a second tubular portion having an outside diameter greater than the inside diameter of the front end of the tubular portion of the trocar tube in the usual state and a grip member attached to the rear end of the second tubular portion. By this structure, the trocar tube permits the insertion of various kinds of operative devices.

Since the trocar needle 70 and the trocar tube 10 become gradually smaller in outside diameter toward the front end, the resistance when they are thrust into the body wall is small.

Since the front end of the trocar tube 10 is located at or behind the neck of the trocar needle 70, the front end 22 of the trocar tube 10 does not catch on the body wall when the trocar is thrust into the body wall, and therefore the pressing force exerted on the body wall and the resistance to the thrust are made smaller. Since the front end 22 of the trocar tube 10 can be expanded by the tapered portion 74 of the trocar needle 70 when the trocar needle 70 is slowly extracted, the extraction of the trocar needle 70 from the trocar tube 10 is made easy.

What is claimed is:

1. A trocar tube comprising a tubular portion and a grip attached to a rear end of said tubular portion, the grip having an insertion opening, and said tubular portion being smaller in diameter at a front end than at the rear end in an original state of the trocar tube, and said tubular portion being constructed so that a front end portion of said tubular portion is expandable from an original diameter in the original state when a device having an outside diameter greater than an inside diameter of said front end of said tubular portion is inserted into the tubular portion by way of the insertion opening, said tubular portion of said trocar tube comprising a plurality of strips and an elastic tube, the strips being arranged substantially in a cone shape which becomes gradually smaller in outside diameter from a rear end to a front end, the strips each having an outside surface and a pair of sides, the elastic tube covering at least the outside surface of the strips, and the sides of adjacent ones of said strips being unsecured to each other.

2. A trocar tube of claim 1 wherein the tubular portion is constructed so that said front end portion of said tubular portion returns to the original diameter after removal of the device.

3. A trocar tube of claim 1 wherein said front end portion of said tubular portion is expandable to about the same inside diameter as the rear end of the tubular portion.

4. A trocar tube of claim 1 wherein said front end portion of said tubular portion is expandable to about the same cross-sectional area as the rear end of the tubular portion.

5. A trocar tube of claim 4 wherein said front end portion of said tubular portion is expandable to a larger cross-sectional area upon insertion of the device into said tubular portion.

6. A trocar tube of claim 1 wherein gaps between the sides of adjacent ones of said plurality of strips widen when said elastic tube expands upon insertion of the device into said tubular portion.

7. A trocar tube of claim 1 wherein each of said strips possesses a trapezoidal shape with a front end of each strip being smaller in width than a rear end.

8. A trocar tube of claim 1 wherein the device is an expanding device for expanding said trocar tube or an operation device.

9. A trocar of claim 8 wherein said expanding device for expanding said trocar tube comprises a tubular member having an outside diameter greater than the inside diameter of the front end of said tubular portion of said trocar tube in the original state and a grip member attached to a rear end of said tubular member.

10. A trocar comprising:
a trocar tube which comprises a tubular portion and a grip attached to a rear end of said tubular portion, said grip having an insertion opening, said tubular portion being smaller in diameter at a front end than at the rear end in an original state, and said tubular portion being constructed so that a front end portion of said tubular portion is expandable from an original diameter in the original state when device having an outside diameter greater than an inside diameter of said front end of said tubular portion is inserted into the tubular portion by way of the insertion opening, and
a trocar needle which comprises a shaft, a piercing end provided at a front end side of said shaft, and a grip member attached to a rear end side of said shaft, said shaft becoming gradually smaller in diameter toward the front end side, said trocar needle having a neck formed at a rear of said piercing end, said neck being formed by a tapered portion which is provided towards a rear end portion of said piercing end and which becomes gradually larger in outside diameter toward a tip end of said piercing end.

11. A trocar of claim 10 wherein said tubular portion has a lumen said shaft having a front end and a rear end, said shaft of said trocar needle being substantially cone shaped so that the needle becomes gradually smaller from the rear end of the shaft to the front end of the shaft, said needle being shaped closely similar to a form of the lumen of said tubular portion in the original state.

12. A trocar of claim 10 wherein said tubular portion is substantially cone shaped so that the tubular portion becomes gradually smaller in outside diameter from the rear end to the front end.

13. A trocar of claim 10 wherein said tubular portion is constructed so that the front end portion of said tubular portion returns to the original diameter after removing the device.

14. A trocar of claim 10 wherein said front end portion of said tubular portion is expandable to about the same inside diameter as the rear end of the tubular portion.

15. A trocar of claim 10 wherein said front end portion of said tubular portion is expandable to about the same cross-sectional area as the rear end of the tubular portion.

16. A trocar of claim 10 wherein said front end portion of said tubular portion is expandable to a larger cross-sectional area upon insertion of the device into said tubular portion.

17. A trocar of claim 10 wherein said tubular portion of said trocar tube comprises a plurality of strips each having an outside surface and an elastic tube which covers at least the outside surface of the strips.

18. A trocar of claim 17 wherein said plurality of strips are arranged to form a tube, with sides of adjacent ones of said strips being unsecured.

19. A trocar of claim 17 wherein gaps between the sides of adjacent ones of said plurality of strips widen when said elastic tube expands upon insertion of the device into the tubular portion.

20. A trocar of claim 17 wherein each of said strips possesses a trapezoidal shape having a front end smaller in width than a rear end.

21. A trocar of claim 10 wherein said device is an expanding device for expanding said trocar tube or an operation device.

22. A trocar of claim 21 wherein said expanding device for said trocar tube comprises a tubular member having an outside diameter greater than the inside diameter of the front end of said tubular portion of said trocar tube in the original state and a grip member attached to a rear end of said tubular member.

23. A trocar tube of claim 10 wherein said tubular portion of said trocar tube comprises a plurality of strips each having an outside surface and an elastic tube which covers at least the outside surface of the strips, the sides of adjacent ones of said strips being unsecured to each other.

24. A trocar tube of claim 10 wherein said tubular portion of said trocar tube comprises a plurality of strips and an elastic tube, the strips being arranged substantially in a cone shape which becomes gradually smaller in outside diameter from a rear end to a front end, the strips each having an outside surface and a pair of sides, the elastic tube covering at least the outside surface of the strips, the sides of adjacent ones of said strips being unsecured to each other.

25. A trocar comprising:

a trocar tube which comprises a tubular portion and a grip attached to a rear end of said tubular portion, said grip having an insertion opening, said tubular portion being smaller in diameter at a front end than at the rear end in an original state, said tubular portion of said trocar tube comprising a plurality of strips and an elastic tube, the strips being arranged substantially in a cone shape which becomes gradually smaller in outside diameter from a rear end to a front end, the strips each having an outside surface and a pair of sides, the elastic tube covering at least the outside surface of the strips, and the sides of adjacent ones of said strips being unsecured to each other, a trocar needle which is inserted into said trocar tube and comprises a shaft, a piercing end provided at a front end side of said shaft and projecting towards a front end of said trocar tube, and a grip member attached to a rear side of said shaft, said shaft becoming gradually smaller in diameter toward the front end, an expanding device insertable into the tubular portion by way of the insertion opening for expanding said trocar tube and for use after removing said trocar needle from said trocar tube, said expanding device comprising a tubular member having an outside diameter greater than the inside diameter of the front end of said tubular portion of said trocar tube, and a grip member attached to a rear end of said tubular member, said tubular portion having a front end portion that is expandable upon insertion of the expanding device into the insertion opening.

26. A trocar of claim 21 wherein said trocar needle has a neck for supporting the front end of said trocar tube, the neck being formed at a rear of said piercing end.

27. A trocar of claim 25 wherein gaps between the sides of adjacent ones of said plurality of strips widen when said expanding device is inserted into the tubular portion and said elastic tube expands upon insertion of said expanding device into the tubular portion.

28. A trocar tube of claim 21 wherein said grip of said trocar tube is provided with a valve, said valve comprising a slit valve member provided with a slit which closes to retain airtightness when said expanding device is not inserted into the insertion opening and expands when the expanding device is inserted into the insertion opening, and a sealing member for sealing a gap between an inside surface of the insertion opening and the expanding device when the expanding device is inserted into the insertion opening.

* * * * *

UNITED STATES PATENT AND TRADEMARK OFFICE
CERTIFICATE OF CORRECTION

PATENT NO. : 6,162,236
DATED : December 19, 2000
INVENTOR(S) : Toshihiko Osada

It is certified that error appears in the above-identified patent and that said Letters Patent is hereby corrected as shown below:

Title page,
Item [22] should read:

[22]   July. 9, 1997

Column 4,
Line 20, "aibrementioned" is changed to -- aforementioned --.
Line 42, "therst" is changed to -- thrust --.

Column 13,
Line 42, "40" is changed to -- 4.0 --.

Column 15,
Line 31, delete "encan" and insert -- resin can be --.

Column 16,
Line 1, "dimeter" is changed to -- diameter --.

Column 18,
Line 25, "dif&&rent" is changed to -- different --.

Column 19,
Line 19, "iflicted" is changed to -- inflicted --.

Column 20,
Line 36, "to" is changed to -- trocar --.
Line 58, "chnracterized" is changed to -- characterized --.

Claim 26,
Line 1, "21" is changed to -- 25 --.

UNITED STATES PATENT AND TRADEMARK OFFICE
CERTIFICATE OF CORRECTION

PATENT NO. : 6,162,236
DATED : December 19, 2000
INVENTOR(S) : Toshihiko Osada

It is certified that error appears in the above-identified patent and that said Letters Patent is hereby corrected as shown below:

<u>Claim 28,</u>
Line 1, "21" is changed to -- 25 --.

Signed and Sealed this

Twenty-third Day of October, 2001

Attest:

*Nicholas P. Godici*

NICHOLAS P. GODICI
*Acting Director of the United States Patent and Trademark Office*

*Attesting Officer*